United States Patent
Graber et al.

(12)

(10) Patent No.: US 6,251,419 B1
(45) Date of Patent: Jun. 26, 2001

(54) MEMBRANE SYSTEM FOR CONTROLLED TISSUE REGENERATION IN CASES OF DISEASES OF THE PERIODONTIUM

(76) Inventors: Hans Georg Graber, Bleiberger Strasse 160, 52074 Aachen (DE); Friedrich Lampert, Ardennenstrasse 21, 52026 Aachen (DE)

( * ) Notice: Subject to any disclaimer, the term of this patent is extended or adjusted under 35 U.S.C. 154(b) by 0 days.

(21) Appl. No.: 09/403,582

(22) PCT Filed: Apr. 17, 1998

(86) PCT No.: PCT/DE98/01089

§ 371 Date: Jan. 5, 2000

§ 102(e) Date: Jan. 5, 2000

(87) PCT Pub. No.: WO98/47480

PCT Pub. Date: Oct. 29, 1998

(30) Foreign Application Priority Data

Apr. 22, 1997 (DE) .............................. 197 16 815
Nov. 4, 1997 (DE) .............................. 197 48 688

(51) Int. Cl.⁷ ....................................... A61F 2/00
(52) U.S. Cl. .................. 424/424; 424/422; 424/435; 433/215; 433/222.1; 514/900

(58) Field of Search ................................ 433/222.1, 215, 433/201.1; 424/491, 435, 424, 422, 460

(56) References Cited

U.S. PATENT DOCUMENTS

| 4,603,695 | | 8/1986 | Ikada et al. ...................... 128/334 R |
| 4,961,707 | | 10/1990 | Magnusson et al. ................. 433/215 |
| 5,635,601 | * | 6/1997 | Moyle et al. ..................... 530/388.2 |
| 5,804,263 | * | 9/1998 | Goldberg et al. ................... 428/34.7 |

FOREIGN PATENT DOCUMENTS

| 195 40 658 A1 | 5/1996 | (DE) | ................................ C08J/7/06 |
| 0 793 965 A2 | 9/1997 | (EP) | ............................. A61K/38/04 |
| 0 793 965 A3 | 9/1997 | (EP) | ............................. A61K/38/04 |
| 90/07308 | 7/1990 | (WO) . |
| 90/11730 | 10/1990 | (WO) . |
| 96/15795 | 5/1996 | (WO) . |

* cited by examiner

*Primary Examiner*—James M. Spear
*Assistant Examiner*—Liliana Di Nola-Baron
(74) *Attorney, Agent, or Firm*—Steven J. Hultquist; William A. Barrett; Marianne Fuierer

(57) ABSTRACT

The invention relates to a membrane system for controlled tissue regeneration of the periodontium, comprising a resorbable polymer membrane and anti-adhesion molecules.

16 Claims, No Drawings

MEMBRANE SYSTEM FOR CONTROLLED TISSUE REGENERATION IN CASES OF DISEASES OF THE PERIODONTIUM

This application is the national stage of PCT/DE98/01089, filed Apr. 19, 1990.

The present invention relates to a membrane system for the treatment of periodontitis.

Also because of uncontrolled growth of the absorbing epithelium towards the tip of the root and the formation of gingival sulci, the inflammation of the gingiva, caused by microbial plaque, will result in a step-wise loss of peridontal tissue accompanied by loss of teeth if it is not treated. The alveolar bone, root cementum and desmodontal fibrous apparatus or fibers are affected by this. The presently only regenerative parodontitis treatment consists in an operation serving for removal of the gingival sulci, subsequent thorough cleaning of the affected sites and application of a membrane consisting of expanded polytetrafluoroethylene (e-PTFE, Gore-Tex) around the dental neck. Thereafter, the gingiva is returned into its original position and the implant is covered. In a second operation, the implant is removed again after about 4 to 6 weeks. The drawbacks of this method are a possible bacterial colonization of the membrane accompanied by impaired wound healing as well as the long-winding and painful procedure comprising two operations.

Therefore, the object of the present invention consists in the provision of a product which avoids the above drawbacks occurring in connection with a parodontitis treatment. This object is achieved by a membrane system according to claim 1. Advantageous embodiments follow from the subclaims.

In particular, the membrane system according to the invention includes a resorbable polymer membrane as well as anti-adhesion molecules.

Any physiologically safe polymer which is known from dentistry and general medicine and degradable, i.e. resorbable, by the body is suitable as a resorbable polymer membrane. In particular, poly(D,L-lactide), poly(D,L-lactide-co-trimethylene carbonate), poly(ethylene-co-propylene), poly(ethylene-co-vinyl acetate) and poly(D,L-lactide-co-glycolide) and the blends or mixtures thereof are particularly suitable. They can be purchased (e.g. from the company of Boehringer Ingelheim). The polymers can be surface-modified preferably by common methods to improve the cell adhesion. For example, the plasma-induced graft copolymerization with 2-hydroxyethyl methacrylate or the graft copolymerization with acrylic acid and subsequent covalent attachment of fibronectin are suitable for this purpose.

All molecules which compensate the effect of adhesion molecules are suitable as anti-adhesion molecules. Adhesion molecules are generally understood to mean molecules which play an essential part in the cell-to-cell communication and cell-to-matrix communication, in particular they are understood to mean the integrins which were also identified in the periodontium (Steffensen et al., J. Periodontol. 1992, 63: 584–592). For compensating the effect exerted by the adhesion molecules, competitive proteins and peptides, respectively, are suited for this purpose (what is called disintegrins or disintegrin-like proteins and peptides, respectively) as well as antibodies directed against the adhesion molecules, which can be purchased. Examples are monoclonal mouse antibodies against the integrin subunit α5 (clone IOP 49c; Immunotech, Marseille), integrin subunit β-4 (clone 3E1; Biomol, Hamburg), integrin subunit α-6 (clone GoH3; Dianova, Hamburg), and integrin subunit β-1 (clone P4c10; Biomol, Hamburg). In particular, monoclonal antibodies directed against the integrin subunits α-6 and β-1 are suitable, separately and as a mixture.

The anti-adhesion molecules are applied onto, and inserted in, respectively, the polymer membrane by methods known to a person skilled in the art. This can be done for the covalent surface bond of the anti-adhesion molecules e.g. by the carbodiimide method. Another possibility is the mixing of the anti-adhesion molecules with the polymer components for the polymer production or the subsequent surface modification by means of plasma-induced graft copolymerization. For the well-calculated release of the anti-adhesion molecules, the polymer membrane systems are equipped therewith in locally differing manner.

Also because of uncontrolled growth of the absorbing epithelium towards the tip of the root, the inflammation of the gingiva, caused by microbial plaque, results in a shift of the epithelial line towards the tip of the root, so that a regeneration of the collagen fibers is prevented and the fixing function of the periodontium is thus restricted. Of the adhesion molecules, particularly the integrins are responsible for the adhesion of the cells to the basal membrane. They bind to the extracellular matrix thus effecting a modification of the intracellular gene expression, a modification of the cellular proliferation and differentiation. In epithelial wound healing, particularly the integrin subunits α-6 and β-1 serve for connecting the keratocytes migrating into the wound region with all extracellular matrix proteins of the basal membrane. The invention is now based on the fact that growth inhibition of the epithelium and growth stimulation shall simultaneously take place in the connective tissue. This serves for supporting regeneration of the functional periodontium and accelerated wound healing. According to the invention the membrane system is placed around the dental neck or the dental necks where the development of parodontitis threatens or where a first operation has already been made to remove the gingival sulci formed. In the latter case, the above described second operation can then be avoided by means of the membrane system according to the invention. A continuous membrane or a system consisting of several membrane subunits can be used. It is preferred that the anti-adhesion molecules are only located in the membrane region where they become neighbors of the absorbing epithelium. In this connection, an active substance concentration shall be achieved as a function of the anti-adhesion molecule used. For example, 1:40 to 1:400 dilutions of antibodies are used against the integrin subunits α-6 and β-1.

In a preferred embodiment, the membrane system according to the invention also contains growth factors and/or cytokines to stimulate in well-calculated fashion the growth of the periodontium connective tissue for developing an efficient periodontium. The suitable growth factors are those with which a person skilled in the art is familiar, such as TGF-β or EGF. The cytokines to be mentioned are e.g. the colony-stimulating factors (CSF), interleukins and interferon-γ. The growth factors and/or cytokines are inserted in and attached to, respectively, the polymer membrane in a way the same as that described above for the anti-adhesion molecules. For them it is also advantageous to be located only on those sites of the membrane system where they can influence said parts of the periodontium.

In a preferred embodiment, the membrane system according to the invention also contains antibiotics. These antibiotics serve for preventing colonization of the membrane and the jaws by bacteria and having the wound healing process proceed without bacterial inflammation. Basically all usable antibiotics known to a person skilled in the art in the oral and dental medicine are suitable as antibiotics. These are particularly antibiotics which relate to the anaerobic range of germs, such as tetracyclines, metronidazole, macrolide antibiotics, quinolones, lincomycins, and chloramphenicol, and can be used in combination with conventional antibiotics, such as penicillins. Metronidazole is particularly preferred. Like the growth factors and cytokines, respectively, and the anti-adhesion molecules, the antibiotics are also inserted in and attached to, respectively, the polymer membrane. However, they are preferably disposed throughout the membrane system to achieve an area-wide full antibacterial effect. In this connection, an active substance concentration of about 500 to 2,000 ppm, particularly about 1,000 ppm, is effective in the serum level.

Thus, the present invention is perfectly suited for the method known under the term of "guided tissue regeneration" (GTR) to eliminate periodontal defects.

The invention is further explained by the below example.

EXAMPLE

Biopsies of marginal gingiva, comprising oral epithelium and sub-epithelial connective tissue, are cultured in fragments of 1 to 2 mm$^2$ at 37° C. in 24-well microtiter trays with RPMI 1640 medium supplemented with L-glutamine, 10% FCS, 50 μg/ml gentamcyin, 0.31 μg/100 ml insulin and 5 μg/ml hydrocortisone. The fragments were divided into groups and the procedure was as follows:

I) without the addition of antibodies

II) with the addition of irrelevant control antibodies (mouse-anti-rat immunoglobulin NK 212-005-102; Dianova, Hamburg, concentration 1.8 mg/ml)

III) addition of antibodies against integrin subunit β-1 (clone GoH3; Dianova, Hamburg)

IV) addition of antibodies against integrin subunit α-6 (clone P4-c10; Biomol, Hamburg)

V) addition of antibodies against both integrin subunits in combination

In amounts of 1:400 each, the antibodies were diluted in culture medium and added.

With daily change of medium and after uniform culture period of 8 days, histological and immunohistological preparation was carried out with cryostat cuts of the fragments.

The following evaluations were made: 1st the epithelial formation on the wound matrix, 2nd expression of epithelial integrins, and 3rd receptor-blocking antibody responses.

While a complete epithelialization could be observed in control groups I and II (without and with irrelevant antibodies), epithelium migration could be inhibited by successful integrin blocking of α-6 and β-1, the combination of both antibodies (group V) supplying the best results.

What is claimed is:

1. A membrane system for the controlled tissue regeneration of the periodontium, comprising a resorbable polymer membrane, said membrane comprising:

(a) a first antibody which binds to an integrin α subunit; and (b) a second antibody, which binds to an integrin β subunit;

wherein either the first antibody binds to the α-6 subunit and/or the second antibody binds to the β-1 subunit.

2. The membrane system according to claim 1, wherein the resorbable polymer is selected from the group consisting of: poly(D,L-lactide), poly(D,L-lactide-co-trimethylene carbonate), poly(ethylene-co-propylene), poly(ethylene-co-vinyl acetate) and poly(D,L-lactide-co-glyoclide) and the blends or mixtures thereof.

3. The membrane system according to claim 1, wherein the membrane further comprises anti-adhesion molecules selected from the group consisting of proteins and peptides competitive with respect to adhesion molecules and antibodies directed against adhesion molecules.

4. The membrane system according to claim 1, wherein the membrane system further comprises a component selected from the group consisting of growth factors and cytokines.

5. The membrane system according to claim 4, wherein the component is TGF-β1.

6. The membrane system according to claim 1 wherein the membrane system further comprises one or more antibiotics.

7. The membrane system according to claim 6, wherein the one or more antibiotics comprise metronidazole.

8. The membrane system of claim 1 wherein the resorbable polymer membrane is treated with antibodies by the carbodiimide method.

9. The membrane system of claim 1 wherein the antibodies are mixed with the polymer components of the resorbable membrane.

10. The membrane system of claim 1 wherein the surface of the resorbable polymer membrane is modified with the antibodies by means of plasma-induced graft copolymerization.

11. A method for controlling tissue regeneration of the periodontium comprising applying to the periodontium a membrane comprising a resorbable polymer membrane comprising:

(a) a first antibody, which binds to an α-chain; and (b) a second antibody which binds to an integrin β-chain;

wherein either the first antibody binds to the α-6 subunit and/or the second antibody binds to the β-1 subunit.

12. The membrane system of claim 1 wherein the first antibody binds to an α-6 subunit.

13. The membrane system of claim 1 wherein the second antibody binds to a β-1 subunit.

14. The membrane system of claim 1 wherein the first antibody binds to an α-6 subunit and the second antibody binds to a β-1 subunit.

15. A membrane system for the controlled tissue regeneration of the periodontium, comprising a resorbable polymer membrane, said membrane comprising an antibody that binds to an integrin α-6 subunit.

16. A membrane system for the controlled tissue regeneration of the periodontium, comprising a resorbable polymer membrane, said membrane comprising an antibody that binds to an integrin β-1 subunit.

* * * * *

UNITED STATES PATENT AND TRADEMARK OFFICE
CERTIFICATE OF CORRECTION

PATENT NO. : 6,251,419 B1
DATED : June 26, 2001
INVENTOR(S) : Graber et al.

Page 1 of 1

It is certified that error appears in the above-identified patent and that said Letters Patent is hereby corrected as shown below:

Column 1,
Line 6, "Apr. 19, 1990" should be -- Apr. 17, 1998 --

Signed and Sealed this

Fifth Day of March, 2002

Attest:

JAMES E. ROGAN
*Attesting Officer*    *Director of the United States Patent and Trademark Office*